(12) United States Patent
Janish

(10) Patent No.: US 8,172,813 B2
(45) Date of Patent: May 8, 2012

(54) SYRINGE WITH TWO PIECE PLUNGER ROD

(75) Inventor: James Janish, Garfield, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 100 days.

(21) Appl. No.: 12/393,800

(22) Filed: Feb. 26, 2009

(65) Prior Publication Data
US 2009/0318880 A1 Dec. 24, 2009

Related U.S. Application Data

(60) Provisional application No. 61/032,134, filed on Feb. 28, 2008.

(51) Int. Cl.
*A61M 5/315* (2006.01)

(52) U.S. Cl. ........................................ 604/228

(58) Field of Classification Search .......... 604/218–231, 604/181, 187, 192–198
See application file for complete search history.

(56) References Cited

U.S. PATENT DOCUMENTS

| | | | | |
|---|---|---|---|---|
| 2,283,915 A | * | 5/1942 | Cole | 604/211 |
| 2,658,511 A | * | 11/1953 | Furnell | 604/218 |
| 3,506,008 A | | 4/1970 | Huck | |
| 3,840,007 A | | 10/1974 | Fish | |
| 4,390,016 A | | 6/1983 | Riess | |
| 4,444,335 A | * | 4/1984 | Wood et al. | 222/43 |
| 4,636,202 A | | 1/1987 | Lowin et al. | |
| 4,642,102 A | * | 2/1987 | Ohmori | 604/210 |
| 4,650,468 A | * | 3/1987 | Jennings, Jr. | 604/110 |
| 4,790,822 A | | 12/1988 | Haining | |
| 4,874,385 A | * | 10/1989 | Moran et al. | 604/208 |
| 4,950,251 A | | 8/1990 | Haining | |
| 4,995,869 A | * | 2/1991 | McCarthy | 604/110 |
| 5,135,495 A | | 8/1992 | Arcusin | |
| 5,152,750 A | | 10/1992 | Haining | |
| 5,222,942 A | | 6/1993 | Bader | |
| 5,226,896 A | | 7/1993 | Harris | |
| 5,253,785 A | | 10/1993 | Haber et al. | |
| 5,318,544 A | | 6/1994 | Drypen et al. | |
| 5,344,403 A | | 9/1994 | Lee | |
| 5,376,080 A | * | 12/1994 | Petrussa | 604/198 |
| 5,411,489 A | | 5/1995 | Pagay et al. | |
| 5,531,708 A | | 7/1996 | Woodruff | |

(Continued)

FOREIGN PATENT DOCUMENTS
DE 102005019428 A1 10/2006
(Continued)

OTHER PUBLICATIONS
PCT ISR and Written Opinion for PCT/US2009/035442, (Jun. 5, 2009), 15 pgs.
(Continued)

*Primary Examiner* — (Jackie) Tan-Uyen T. Ho
*Assistant Examiner* — Michael J Anderson

(57) ABSTRACT

Medical devices comprising a syringe barrel, a stopper and a two piece plunger rod are provided. According to one or more embodiments, the two piece plunger rod includes a first plunger rod piece slidably mounted to a second plunger rod piece. The first and second plunger rod pieces include locking elements which allow the length of the plunger rod to be extended during use or injection or compressed during storage or packaging. In one or more embodiments, the medical device is further packaged in a compressed position.

17 Claims, 10 Drawing Sheets

U.S. PATENT DOCUMENTS

| | | | |
|---|---|---|---|
| 6,086,567 A | 7/2000 | Kirchhofer et al. | |
| 6,086,568 A * | 7/2000 | Caizza | 604/218 |
| 6,368,303 B1 * | 4/2002 | Caizza | 604/110 |
| 6,494,863 B1 | 12/2002 | Shaw et al. | |
| 6,583,930 B1 | 6/2003 | Schrenk et al. | |
| 2003/0187400 A1 * | 10/2003 | Liao | 604/195 |
| 2005/0215957 A1 | 9/2005 | Hynes | |
| 2006/0229570 A1 | 10/2006 | Lovell et al. | |
| 2007/0017532 A1 | 1/2007 | Wyrick | |
| 2007/0017533 A1 | 1/2007 | Wyrick | |
| 2007/0244444 A1 | 10/2007 | Guelker et al. | |
| 2008/0015514 A1 | 1/2008 | Burren et al. | |
| 2008/0177236 A1 | 7/2008 | Burren et al. | |
| 2009/0177156 A1 * | 7/2009 | MacLean | 604/135 |

FOREIGN PATENT DOCUMENTS

| | | | |
|---|---|---|---|
| EP | 1323450 A1 | 12/2001 | |
| EP | 1323450 A1 | 7/2003 | |
| EP | 1518574 A2 | 3/2005 | |
| WO | 03020347 A2 | 3/2003 | |
| WO | WO-03/020347 A2 | 3/2003 | |
| WO | 2005011782 A1 | 2/2005 | |
| WO | WO-2005/011782 A1 | 2/2005 | |
| WO | 2006136769 A1 | 12/2006 | |
| WO | WO-2006/136769 A1 | 12/2006 | |
| WO | 2007109450 A2 | 9/2007 | |
| WO | WO-2007/109450 A2 | 9/2007 | |
| WO | WO-2008/068502 A1 | 6/2008 | |
| WO | 2008068502 A1 | 3/2010 | |

OTHER PUBLICATIONS

PCT ISR and Written Opinion for PCT/US2009/035493, (Jun. 18, 2009), 15 pgs.

U.S. Appl. No. 12/393,526, filed Feb. 26, 2009.

International Search Report dated May 6, 2009 (PCT/US2009/035442).

International Search Report dated Jun. 18, 2009 (PCT/US2009/035493).

* cited by examiner

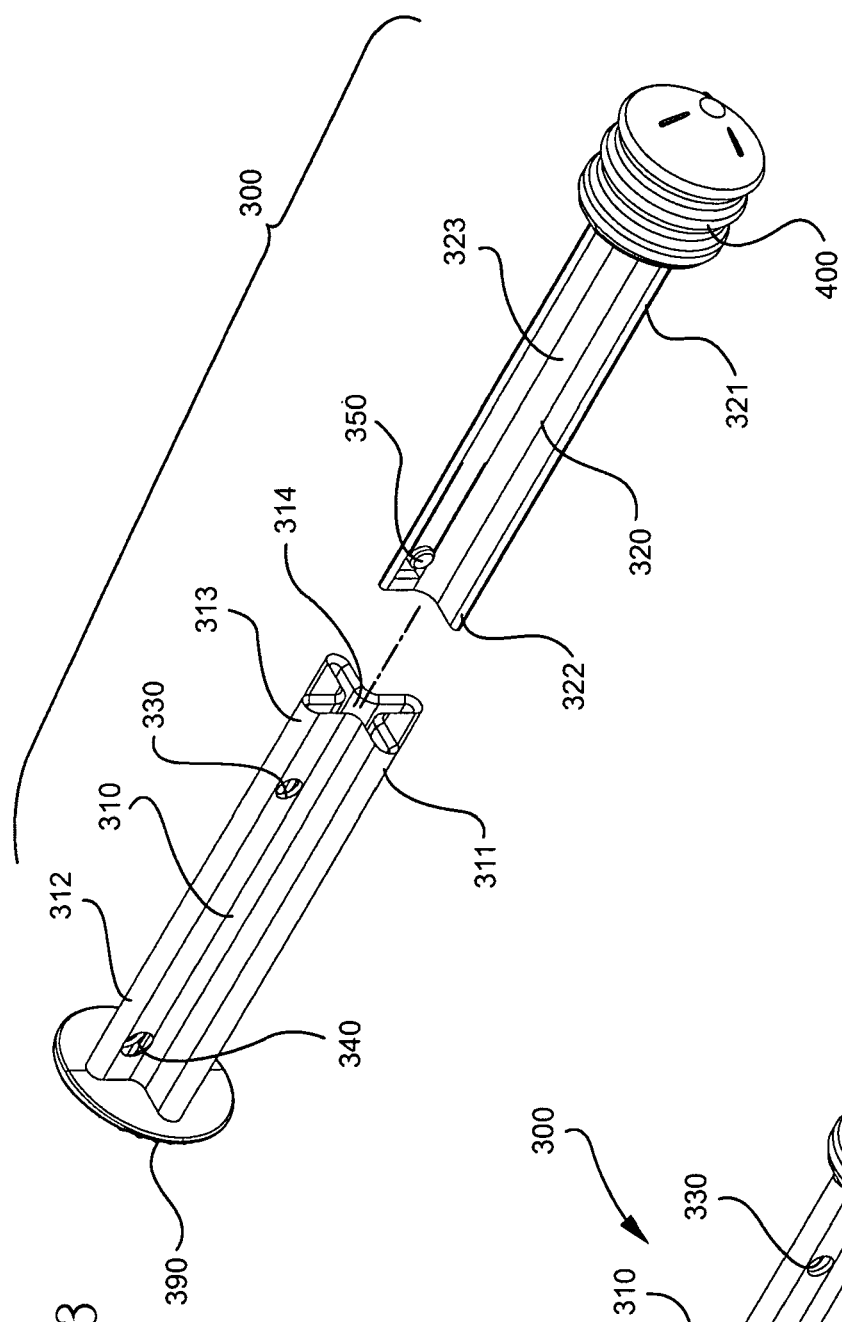
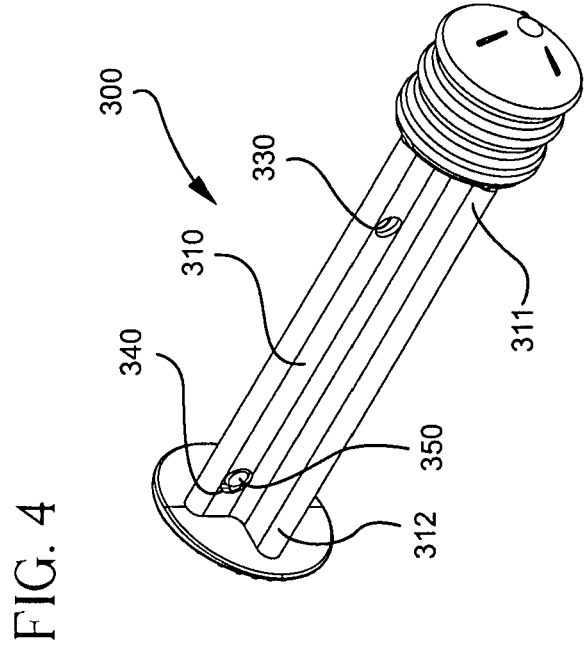

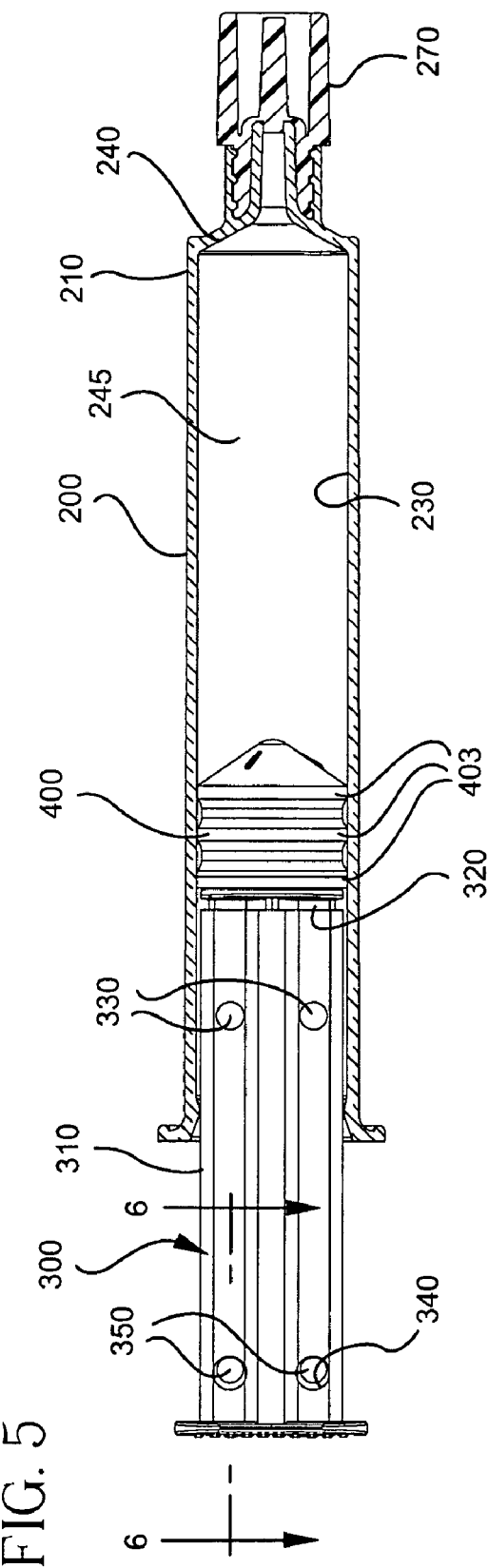

SYRINGE WITH TWO PIECE PLUNGER ROD

CROSS REFERENCE OF RELATED APPLICATION

This application claims the benefit of priority under 35 U.S.C. §119(e) to U.S. Patent Application No. 61/032,134, filed Feb. 28, 2008, which is hereby incorporated by reference in its entirety.

TECHNICAL FIELD

The present invention relates to medical devices having a syringe and two piece plunger rod which allows its length to be compressed and expanded.

BACKGROUND

Syringes generally comprise an elongate single piece plunger rod disposed in a barrel. Generally, the plunger rod is of one piece construction. Syringes that have breakable plunger rods, which break upon application of force into two or more pieces, have been used to prevent reuse of syringes. However, such syringes in which the plunger rod breaks into pieces renders the syringe assembly inoperable because the plunger rod can no longer be advanced within the barrel of the syringe.

In applications where the syringe is prefilled with fluid and then packaged for delivery to the user, the length of the single piece plunger rod must be at least long enough to accommodate the full length of the barrel. Such prefilled syringes act as the storage container for the fluid and must be packaged in such a way to accommodate the prefilled syringe barrel and its full length single piece plunger rod.

While there are a variety of syringe designs available, alternative syringe and plunger rod designs are desirable for various applications and to reduce costs associated with manufacturing and packaging of medical devices.

SUMMARY

In this disclosure, a convention is followed wherein the distal end of the device is the end closest to a patient and the proximal end of the device is the end away from the patient and closest to a practitioner.

One aspect of the present invention pertains to a medical device including a syringe barrel, an elongate two piece plunger rod disposed in the barrel, and a stopper. According to one or more embodiments, the syringe barrel has a side wall with an inside surface that defines a chamber for retaining fluid. In one embodiment, the syringe barrel has an open proximal end and a distal end including a distal wall. The distal wall of an embodiment has a passageway or opening therethrough in fluid communication with the chamber. Some embodiments provide for a chamber pre-filled with fluid. In one or more embodiments, the fluid contained in the chamber is a medical flush solution. In further embodiments, the fluid includes medication.

In one or more embodiments, the syringe barrel has an elongate plunger rod with a distal end and a proximal end disposed therein. In certain embodiments, a stopper can be attached to the distal end of the plunger rod or the stopper can be an integral part of the plunger rod.

The plunger rod according to one or more embodiments has a distal end and a proximal end and is made up of a first plunger rod piece and a second plunger rod piece. The first plunger rod piece is slidably mounted to the second plunger rod piece and allows the plunger rod to be extended from a compressed length to an extended length. The first plunger rod piece may fit inside the second plunger rod piece, which has a hollow cavity to slidably receive the first plunger rod piece. The first plunger rod piece may also have a frame defining a hollor receptacle having a cross-sectional shape. In such embodiments, the second plunger rod has a frame with a complementary cross-sectional shape to the hollow receptacle and may be inserted into the hollow receptacle.

In one or more embodiments, application of an axial force to one or both of the plunger rod pieces allows the first and second plunger rod pieces to move or become moveable with respect to each other from the compressed length to the extended length. In one embodiment, the first and second plunger rod pieces are capable of moving from the compressed length to the extended length with the application of substantially no rotational forces. In accordance with one embodiment, when the first plunger rod piece and second plunger rod piece are extended to the extended length, the syringe is operable to expel fluid when an axial force is applied to the plunger rod in a distal direction. In accordance with one or more embodiments, the medical device is assembled and packaged with the plunger rod in the compressed position in a package.

In accordance with one or more embodiments, the first plunger rod piece has a first locking element and the second plunger rod piece has a second locking element. These locking elements cooperate to fix the plunger rod in the extended length and permit the syringe assembly to be used to expel fluid from the syringe. In one embodiment, the first locking element includes one or more projections or tabs extending outwardly from the first plunger rod piece, which cooperates with a recess, indentation or hole in the second plunger piece into which the first locking element can enter. In further embodiments, the first locking element is a projection or tab biased outwardly from the first plunger rod which enters an indentation, recess or hole on the second plunger rod piece. In yet further embodiments, the locking element includes locking tabs oriented in an inverse relationship with one another so that the locking tabs engage irreversibly upon extending the plunger rod the extended length.

Further aspects of the present invention pertain to a medical device having a syringe with a barrel prefilled with a fluid for delivery to a patient or a medical device. In one or more embodiments, the plunger rod is slidably adjustable between a compressed length and an extended length and is operable to expel the fluid when placed in the extended length.

In one or more embodiments comprising a prefilled syringe, the plunger rod has a distal portion and a proximal portion which are slidably coupled to permit the plunger rod to be adjusted from the compressed length and the extended length. The distal portion is received slidably within the proximal portion of one embodiment. In further embodiments, the proximal portion includes detents and the distal portion includes a recess or opening configured to receive the detents of the proximal portion so that the length of the plunger rod can be adjusted. In yet further embodiments, the detents are disposed on the distal portion while the recess or opening is disposed on the proximal portion. The detents of some embodiments comprise projections that biased radially outwardly to engage a corresponding recess or opening. Some embodiments provide a means for slidably locking the plunger rod to the extended length. In one embodiment, the medical device is enclosed in packaging.

BRIEF DESCRIPTION OF THE DRAWINGS

FIG. 3 shows a disassembled perspective view of a two piece plunger rod according to an embodiment of the invention;

FIG. 4 illustrates the two piece plunger rod and stopper of FIG. 1 in the compressed position according to one or more embodiments of the invention;

FIG. 5 is a cross-sectional view taken along line 5-5 of FIG. 1;

FIG. 6 is an enlarged cross-sectional view taken along line 6-6 of FIG. 5 of a portion of the plunger rod;

DETAILED DESCRIPTION

Figure 1:
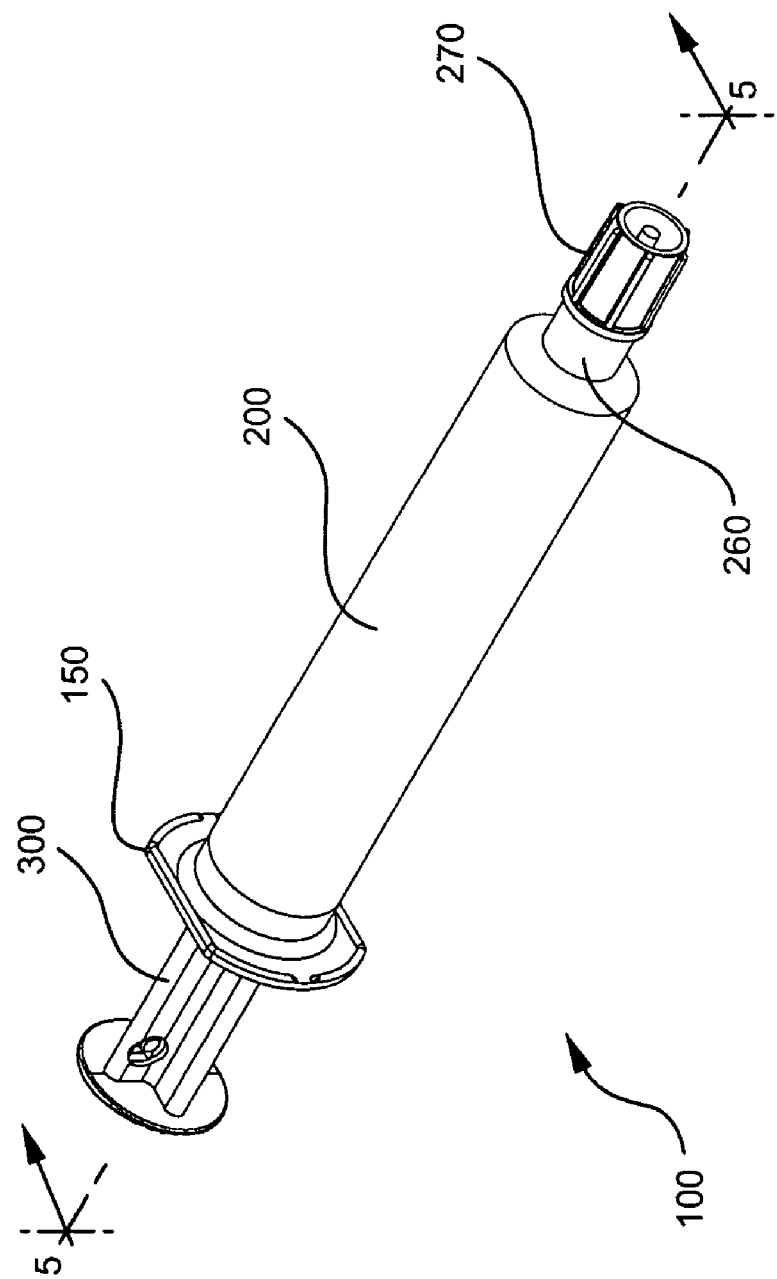
FIG. 1 illustrates a perspective view of a medical device in a compressed position according to an embodiment of the invention.
Figure 2:
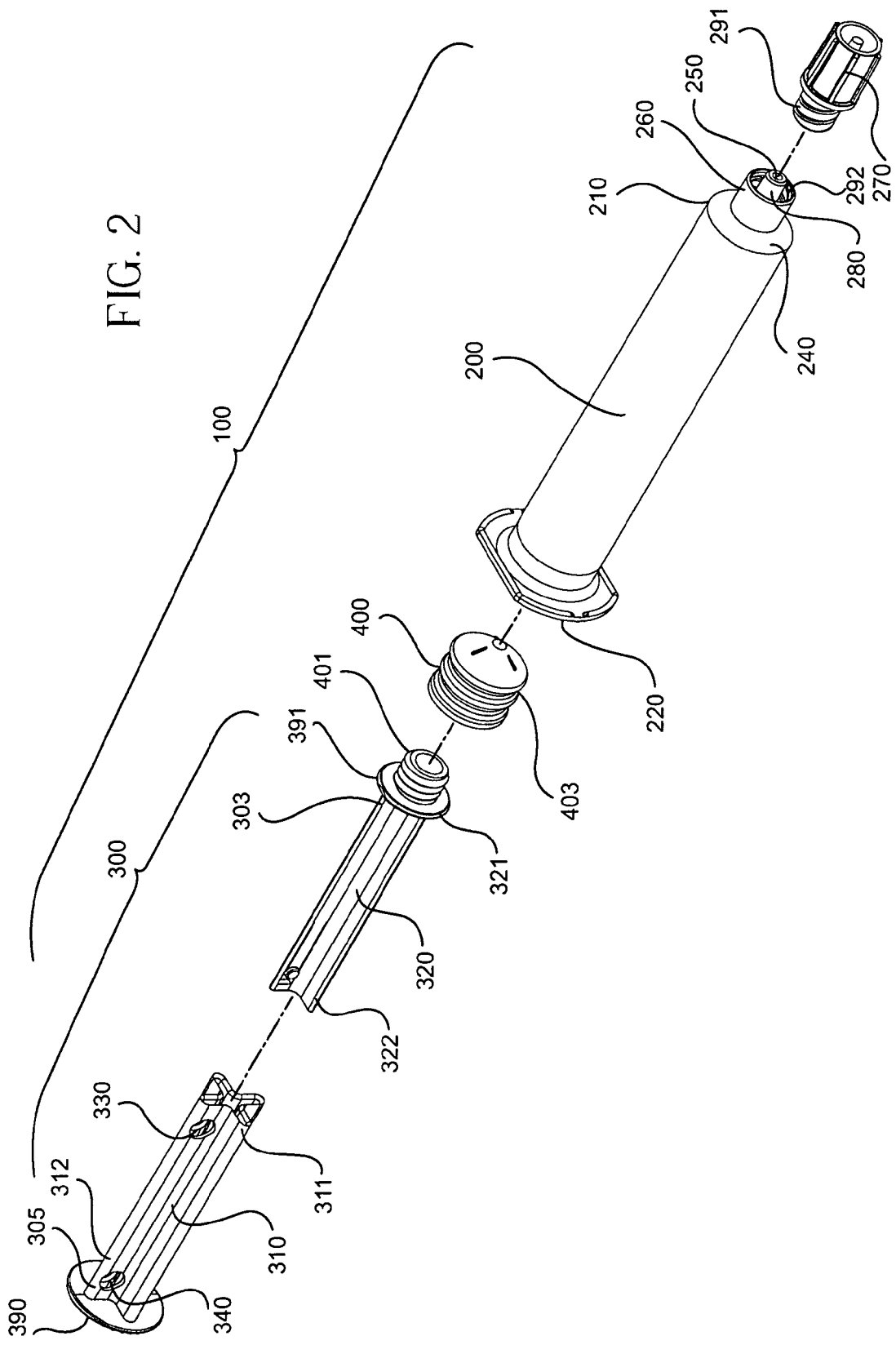
FIG. 2 illustrates a disassembled perspective view of a medical device according to an embodiment of the invention.

Before describing several exemplary embodiments of the invention, it is to be understood that the invention is not limited to the details of construction or process steps set forth in the following description. The invention is capable of other embodiments and of being practiced or being carried out in various ways.

One aspect of the present invention provides for a medical device including a syringe barrel, a plunger rod comprising two pieces and a stopper. The plunger rod according to one or more embodiments has a first plunger rod piece and second plunger rod piece which are slidably engaged to permit adjustment of the length of the plunger rod and permit the plunger rod to be extendible from a compressed length to an extended length or from a compressed position to an extended position.

FIGS. 1-10 show a medical device 100 in the form of a syringe assembly comprising a syringe barrel 200 and a plunger rod 300. In the embodiment shown, the syringe barrel 200 includes a flange 150 at the proximal end of the syringe barrel, which provides the practitioner a gripping surface for the barrel 200 while fluid is being expelled from the syringe. The syringe barrel 200 has a distal end 210, an open proximal end 220, an inside surface 230, which defines a chamber 245 in which fluid may be held and a tip 280. The syringe barrel further includes a distal wall 240 having a passageway or opening 250 in fluid communication with the chamber and the tip 280. The syringe barrel 200 can further include a collar 260 which can provide a means for attaching the cap 270 or a needle hub or other medical device to the syringe barrel, such as a luer-lock collar. Alternatively, tip 280 may have a cap 270 or other medical device connected thereto. As the skilled artisan will understand, the syringe barrel according to certain embodiments may further include a needle hub and needle cannula (not shown) having a lumen attached to the collar 260 and/or tip 280. Such a device including a needle hub and cannula would also include a protective cap (not shown) over the needle cannula.

The distal end of the syringe barrel and cap may include a complementary assembly structure which, as shown in the Figures, is a screw thread 291 on the cap 270 which allow the cap 270 to be removably attached to the syringe having complementary threads 292 on the collar 260. Further examples can include a seal or other means for detecting tampering on the collar, cap and/or syringe barrel.

The plunger rod 300 includes a distal end 303 and a proximal end 305. The plunger rod 300 is comprised of a first plunger rod piece 310 and a second plunger rod piece 320 and a stopper 400 connected to the distal end 303 of the plunger rod 300. The plunger rod 300, when assembled, may be disposed for sliding sealed engagement with the inside surface 230 of the chamber 245. It will be understood that the stopper 400 may be integral with the plunger rod, or it may be provided as shown in the Figures as a separate component that is releasably mounted to the plunger rod 300.

The distal end 303 of the plunger rod 300 includes stopper-receiving threads 401 or other attachment means for releasably attaching the stopper 400 to the plunger rod 300. The stopper 400 includes corresponding threads (not shown), permitting the stopper 400 to be assembled to the plunger rod using a twisting motion. It will be understood that any other suitable releasable attachment mechanism could be used to attach the stopper to the plunger rod. In one or more embodiments, the stopper attachment means includes a male joint while the stopper comprises the female joint. Other embodiments provide for a stopper comprising the male joint while the stopper attachment means comprises the male joint.

The stopper 400 also includes ribs 403 forming a seal with the inside surface 230 of the syringe barrel 200. As otherwise discussed, one or more embodiments of the stopper include threads which allow attachment of the stopper to the plunger rod.

The first plunger rod piece 310 comprises a distal end or portion 311 and a proximal end or portion 312, while the second plunger rod piece 320 comprises a distal end or portion 321 and a proximal end or portion 322. The first plunger rod piece 310 includes a thumb press 390 attached at its proximal end 312. One or more embodiments of the present invention provide for a thumb press having a textured surface. The second plunger rod piece of the plunger rod 320 incorporates a protrusion 391 shown as an annular protrusion between the distal end of the second plunger rod piece 321 and the stopper 400.

As best shown in FIG. 3, the plunger rod 300 comprises two pieces, the first plunger rod piece 310 and the second plunger rod piece 320 being slidably mounted to each other, permitting the overall length of the plunger rod to be adjusted from a compressed length to an extended length. The first plunger rod piece 310 comprises a frame 313 defining a hollow receptacle 314. The second plunger rod piece 320 also has a complementary frame 323 shaped in cross section substantially identical to the first plunger rod piece and is sized and shaped to allow the first plunger rod piece to operate as the female joint and the second plunger rod piece 320 to operate as a male joint that fits in the hollow receptacle 314. This allows the second plunger rod piece to slide proximally and distally when disposed within the hollow receptacle 314 of the first plunger rod piece. The frame 313 of the first plunger rod piece and the frame 323 of the second plunger rod piece can be shaped in the form of a "T" or cross as shown in the Figures or in any other suitable arrangement. In one or more embodiments, the frames 313 and 323 are shaped to prevent rotational movement. In alternative embodiments, the frame may be shaped in the form of a square, rectangle, triangle or any other shape suitable for a plunger rod. Still further embodiments provide for a frame that includes a mechanism or means for preventing rotational movement of the first plunger rod piece and/or second plunger rod piece.

As specifically shown in FIGS. 4 through 7, the second plunger rod piece 320 fits inside the hollow receptacle 314 of the first plunger rod piece 310. It will be understood, of course, that the invention is not limited to the configuration shown. For example, the configuration could be reversed, and second plunger rod piece 320 can comprise a frame defining hollow receptacle and operate as the female joint, while the first plunger rod piece comprises a complementary frame operates as the male joint that fits into the hollow receptacle.

Referring to FIGS. 3 through 7, the first plunger rod piece 310 includes a distal locking recess 330 and a proximal recess 340 disposed near its distal end 311 and proximal end 312, respectively. The recesses 330 and 340 are shown as holes through the frame, but they could also be in the form of indentations or recesses. The second plunger rod piece 320 has proximal locking element 350 disposed near its proximal end 322. The proximal locking element 350 is shown in the form of a projection that extends radially from the frame of the second plunger rod piece 320, and the locking element 350 is shaped complementarily to the recesses 330, 340 on the first plunger rod piece 310.

Figure 7:
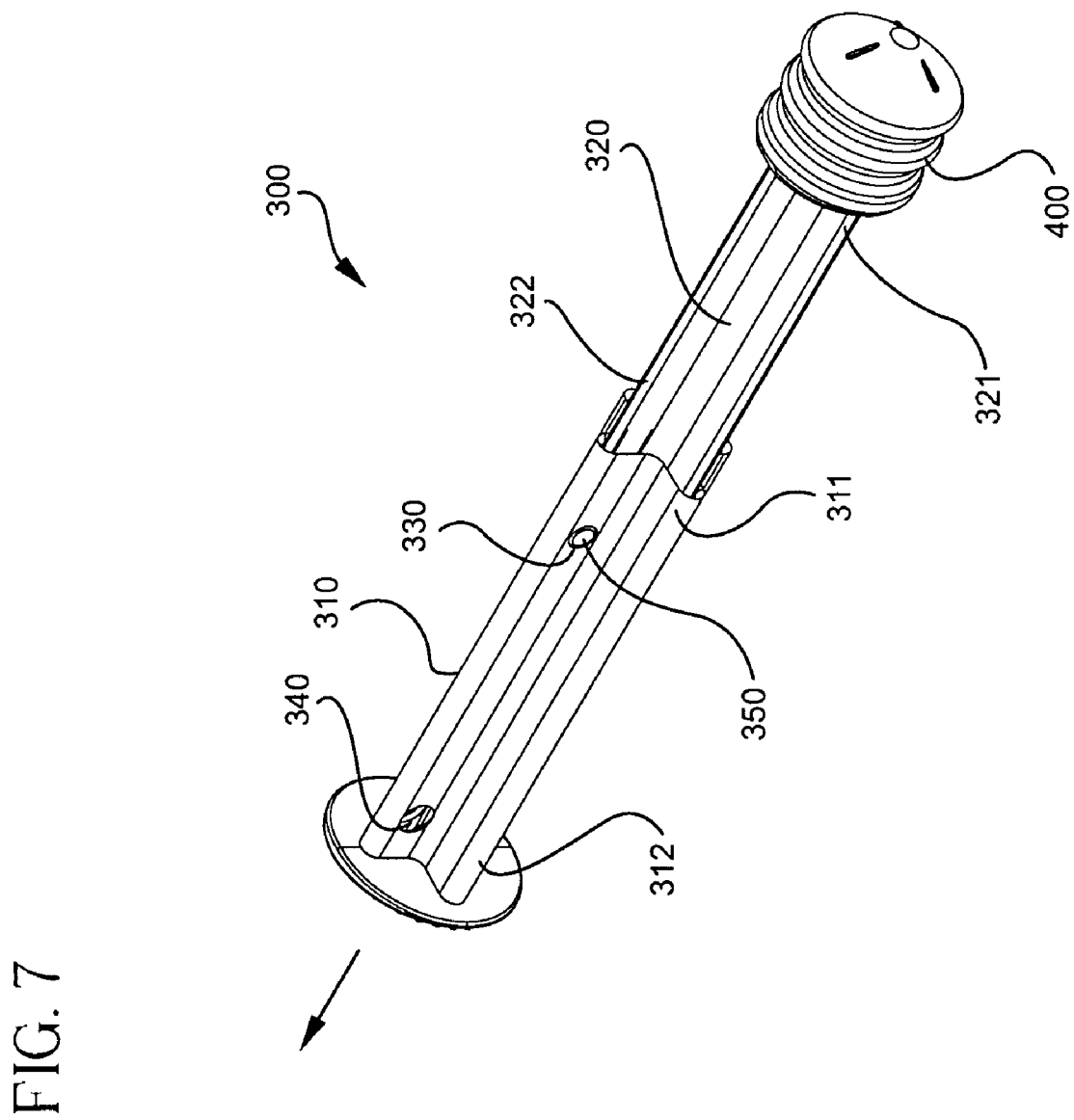
FIG. 7 shows an embodiment of the two piece plunger rod in the extended length position.

In use, with reference to FIGS. 4-10, when the locking element 350 is engaged with the proximal locking recess 340 in the compressed state (as shown in FIG. 4), the cooperation of the locking element 350 and the recess 340 operate to prevent the first and second plunger rod pieces 310, 320 from unintentionally sliding with respect to each other while packaged and prior to use. To deploy the plunger rod into the extended state or configuration as shown in FIG. 7, the user would slide the two plunger rod pieces 310, 320 with respect to each other by pulling on the ends of the pieces until the locking element 350 slides into the distal recess 330, locking the two pieces 310, 320 into an extended length or configuration. Once locked into the extended length or configuration shown in FIG. 7, further relative movement of the two pieces 310, 320 is prevented, unless the user of the device disengaged the locking element 350 from the recess 330.

In the embodiment shown, the cooperating recesses 330, 340 and male locking element 350 are shown as being circular. However, it will be understood that the locking element 350 and recesses 330, 340 can be any suitable shape or in any other configuration that permits the plunger rod to lock in a compressed and extended configuration as shown. Examples of suitable structures include projections, finger-like projections, projections biased outwardly, detents, locking tabs or other projections that cooperate with a complementary element to lock the two plunger rod pieces in place and prevent sliding movement of the plunger rod pieces once they are locked in the extended configuration. In one or more embodiments, the locking element can be a locking tab which is oriented to cooperate with a slot to limit relative movement of the two plunger rod pieces.

In an alternative embodiment, one of either the first plunger rod piece or second plunger rod piece includes two locking elements disposed near the distal and proximal ends, while the other plunger rod piece includes one complementary locking structure positioned near either the distal or proximal ends so that it can engage with the two locking elements on the other piece. In another alternative embodiment, the second plunger rod piece has two openings, while the first plunger rod piece has one projection. In a specific alternative embodiment, the first plunger rod piece has two projections and the second plunger rod piece has one opening. In another alternative embodiment, the second plunger rod piece has two projections and the first plunger rod piece has one opening. In still another alternative embodiment, two locking tabs are provided on either the first plunger rod piece or second plunger rod piece, and one complementary locking tab is provided on the opposite piece. In certain embodiments, the tabs can be biased tabs on one plunger rod piece that cooperate with recesses or other structures on the other plunger rod piece to lock the plunger rod pieces in place. In another alternative embodiment, the female plunger rod piece has an interior annular groove and the male plunger rod piece has a corresponding radially outwardly extending annular ring on the male plunger rod piece that locks the male plunger rod piece into the female plunger rod piece.

Other embodiments of the present invention can include multiple locking elements at different axial positions along the length of the first plunger rod piece and second plunger rod piece to allow the first plunger rod piece and second plunger rod piece to be slidably adjusted to multiple extended and compressed lengths. One or more embodiments also provide for multiple locking elements at different radial positions around the first and second plunger rod pieces.

As shown in the Figures, and in particular FIG. 7, the distal portion 311 of the first plunger rod piece 310 and the proximal portion 322 of the second plunger rod piece overlap 320 when the plunger rod is in the extended position. The overlap provides stability to the two piece plunger rod when the plunger rod is being advanced distally into the barrel of the syringe. The locking elements according to one or more embodiments unlock to allow the first and second plunger rod pieces to slide to the extended position when a user applies an initial axial force in the proximal direction, while preventing further proximal movement beyond the extended position As seen in FIGS. 4-10, the first and second plunger rod pieces are slidably adjustable to allow the length of the plunger rod to be adjusted from a compressed configuration to an extended compressed configuration. In the compressed position, as shown in FIGS. 4-6, the first plunger rod piece 310 slides over the second plunger rod piece 320 until the locking element 350, disposed near the proximal end of the second plunger rod piece 322, enters the proximal recess 340 disposed near the proximal end of the first plunger rod piece 312. The engaged locking element 350 and proximal recess 340 cooperate to fix the plunger rod in the compressed position.

Figure 8:
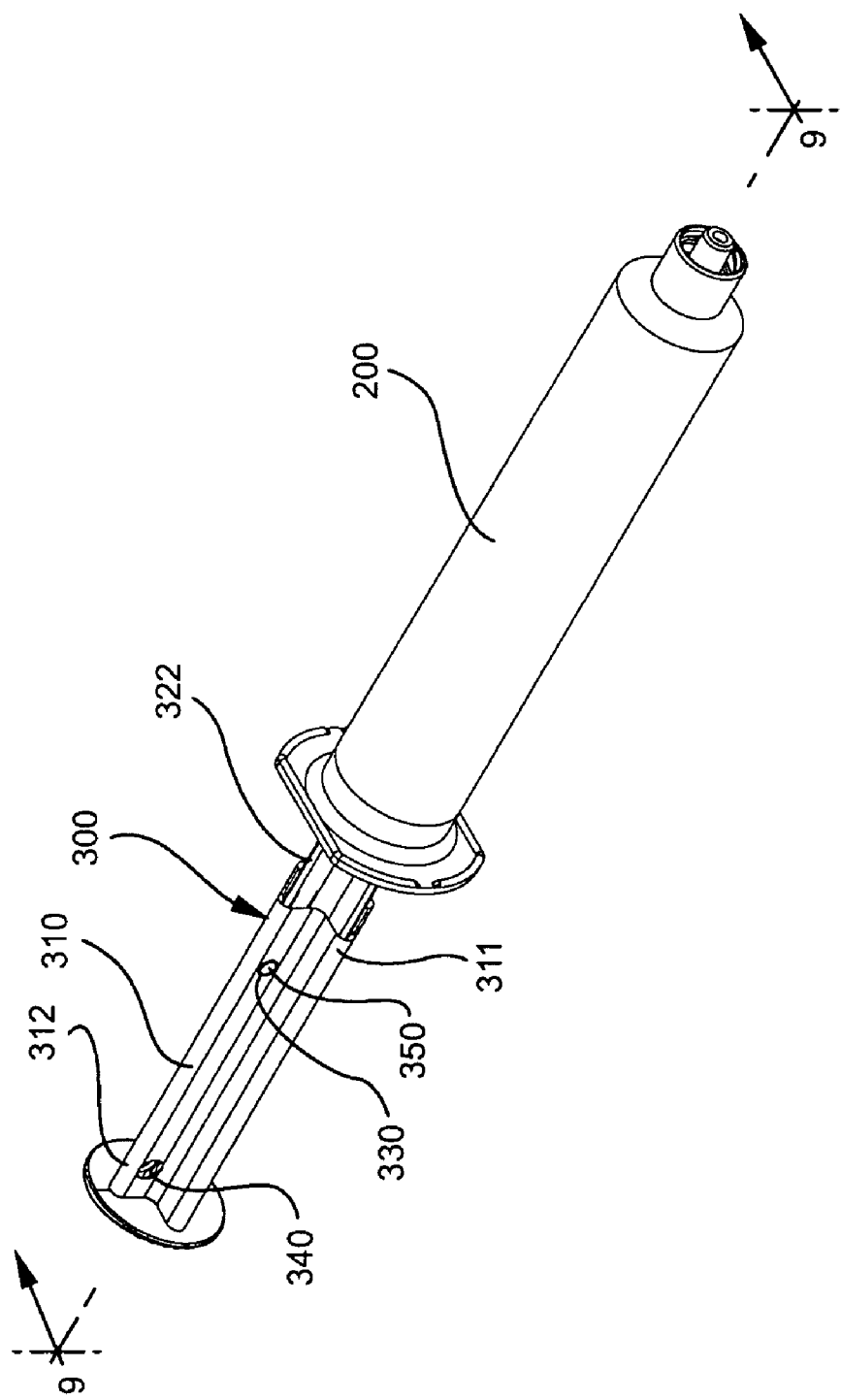
FIG. 8 shows a syringe with an extended two piece plunger rod disposed therein according to one embodiment.
Figure 9:
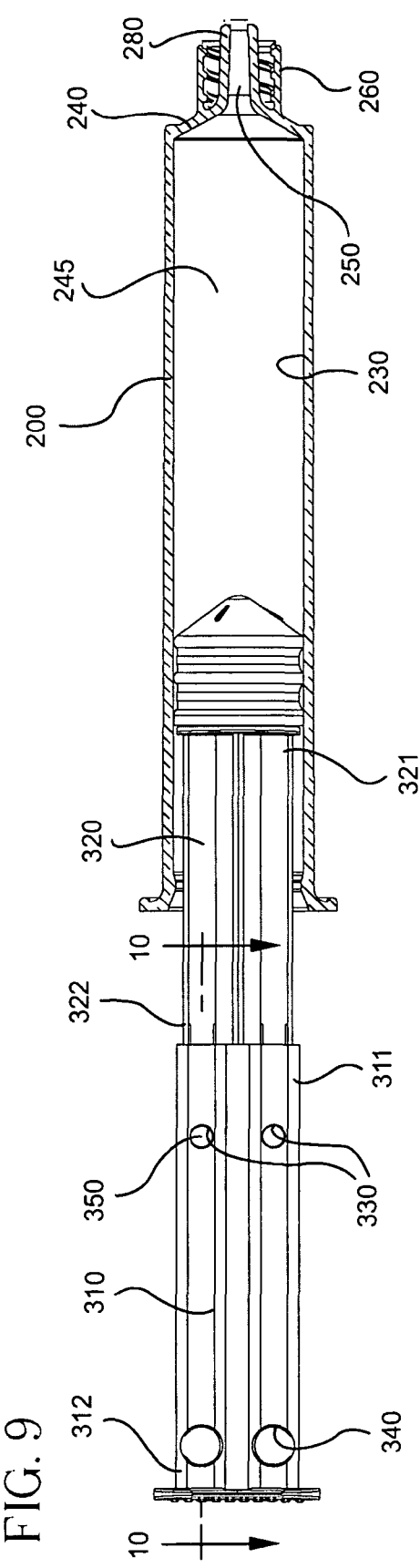
FIG. 9 is a cross-sectional view taken along line 9-9 in FIG. 8.
Figure 10:
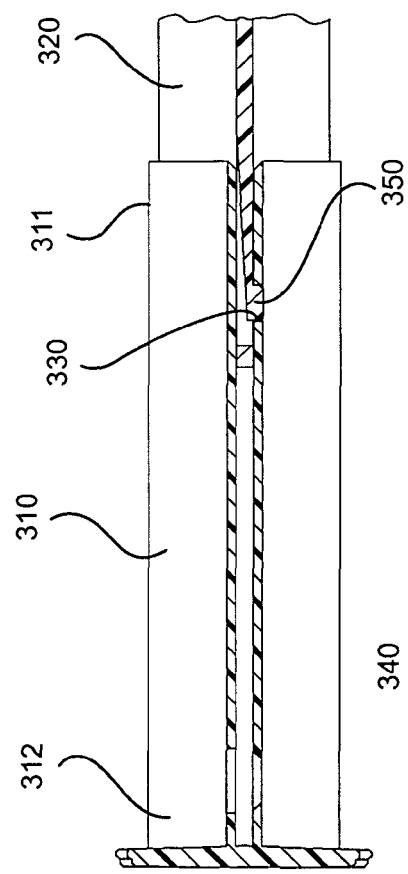
FIG. 10 is an enlarged cross-sectional view of a portion of the plunger rod taken along line 10-10 in FIG. 9.

The device is shown in the extended configuration in FIGS. 8-10. In accordance with one or more embodiments, the device is ready for use when the plunger rod is in the extended configuration. Specifically, upon application of an axial force on the plunger rod pieces opposite directions on each piece, the locking element 350 disposed near the proximal end 322 of the second plunger rod piece 320 disengages from the proximal recess 340 disposed near the proximal end 312 of the first plunger rod piece 310 and allows the first plunger rod piece 310 to slide in the proximal direction relative to the second plunger rod piece 320. Upon application of continuous axial force in the proximal direction, the first plunger rod piece 310 continues to move in the proximal direction until the locking element 350 disposed near the proximal end 322 of the second plunger rod piece 320 engages with the distal recess 330 disposed near the distal end 311 of the first plunger rod piece 310. The first and second plunger rod pieces 310, 320 are fixed in an extended position by the locking elements 330, 350 disposed on their distal and proximal ends 311, 322, respectively. The syringe is now ready for use by applying a distally directed force to the thumb press to move the plunger rod 300 through the barrel 200 of the syringe to expel fluid from the syringe.

Figure 11:
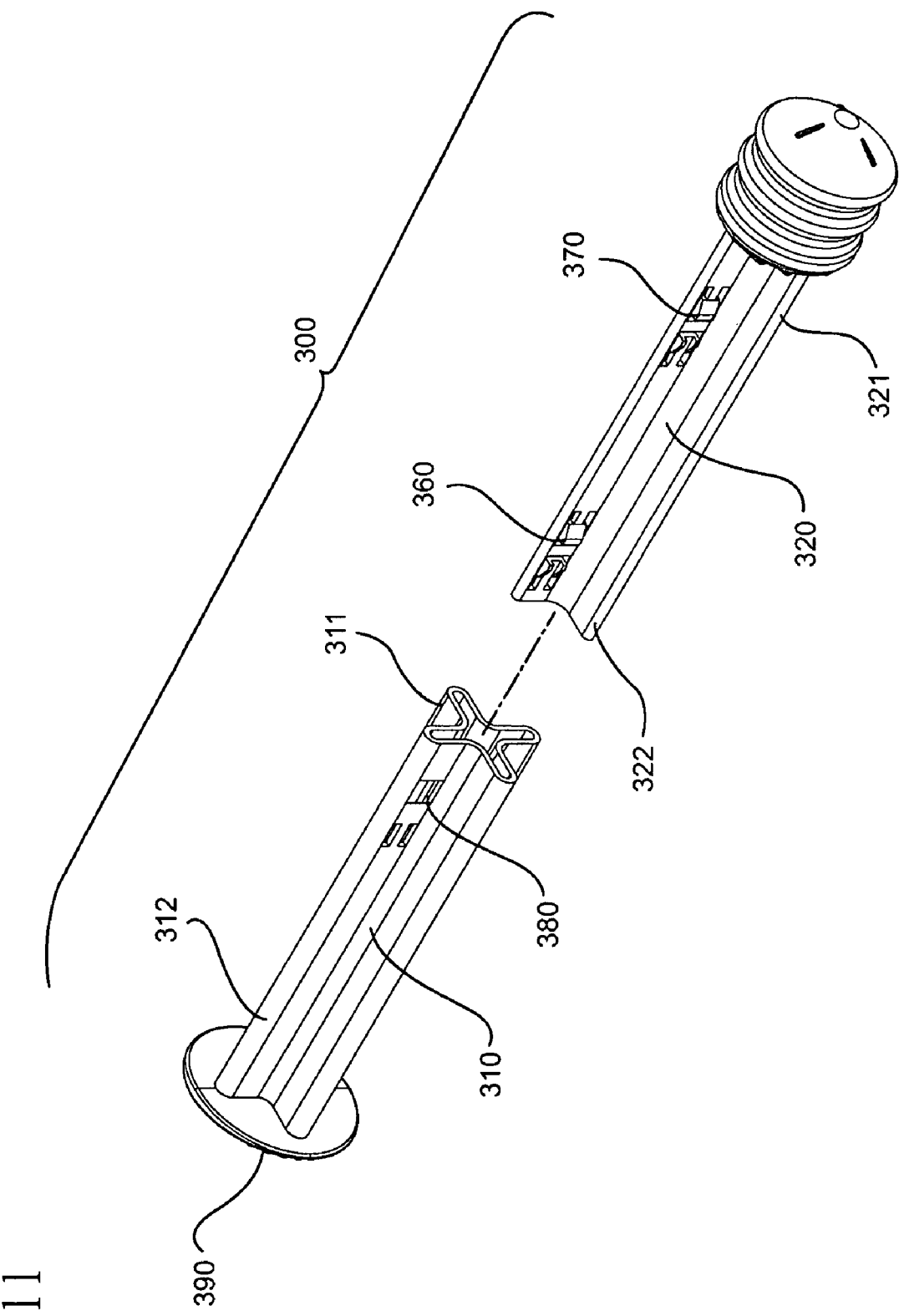
FIG. 11 illustrates the disassembled perspective view of a medical device according to a second embodiment of the invention.
Figure 12:
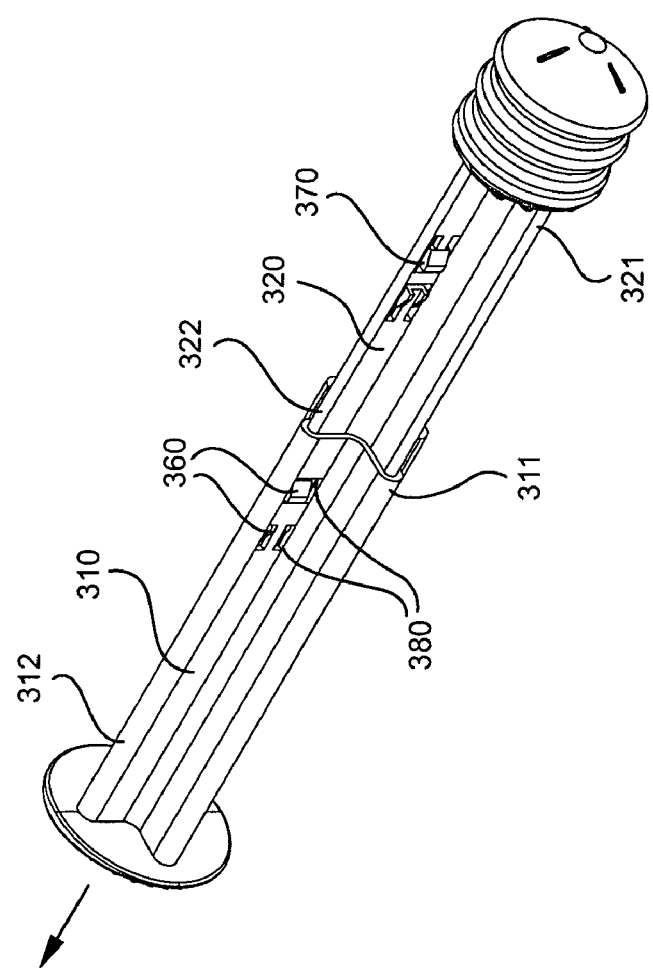
FIG. 12 illustrates a plunger rod and stopper of FIG. 11 in the compressed position.
Figure 13:
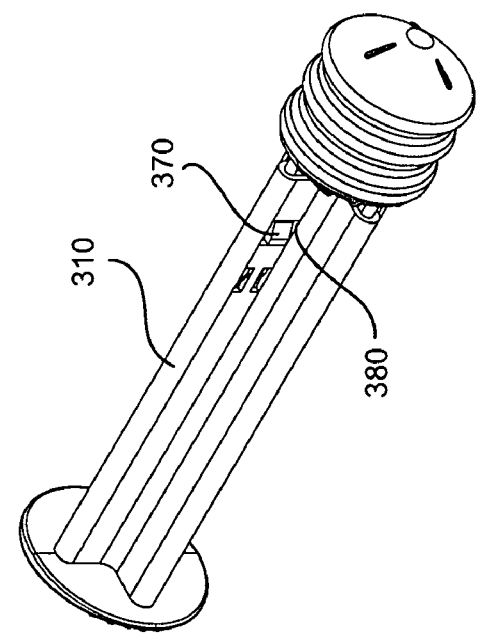
FIG. 13 shows the plunger rod and stopper of FIG. 11 in the extended position.

An alternative embodiment is shown in FIGS. 11-13, which shows a different configuration of locking elements for the two plunger rod pieces. A first pair of radially and outwardly biased tabs or projections 360 are disposed near the proximal end 322 of the second plunger rod piece 320. A second pair of radially and outwardly biased tabs or projections 370 are disposed near the distal end 321 of the second plunger rod piece 320. A pair of recesses 380 that correspond in shape and configuration to the projections 360, 370 are disposed near the distal end 311 of the first plunger rod piece 310, that are configured to lock the two plunger rod pieces 310, 320 in place in the extended and/or locked configuration.

As shown in FIG. 12, the first plunger rod piece 310 can slide over the second plunger rod piece 320 so that the second pair or projections 370 and recesses 380 are engaged when the plunger rod is in the compressed position. Upon application of an axial force in the distal direction to the second plunger rod piece 320, the second pair of projections 370 and recess 380 disengage and the first plunger rod piece 310 slides in the proximal direction relative to the second plunger rod piece 320. As shown in FIG. 13, the first plunger rod piece 310 moves in the proximal direction until the first pair of projections 360, disposed near the proximal end 322 of the second plunger rod piece 320, and recess 380 disposed near the distal end 311 of the first plunger rod piece 310 engage so that the plunger rod is locked in the extended position. Then, similar to the configuration as shown in FIG. 8, the plunger rod can be inserted into the barrel of the syringe and the syringe is ready for use, as the plunger rod pieces are locked in place in the extended configuration.

During a full injection cycle, an axial force in the distal direction is applied to the plunger rod at the thumb press until the stopper is bottomed out in contact with the distal wall of the syringe barrel. The thumb press moves in the distal direction until it is restricted from further movement by the opening 220 at the proximal end of the syringe barrel 200. Accordingly, it is desirable to have a plunger rod having sufficient length to allow bottoming of the stopper. It is believed that in the compressed position, the plunger rod is not long enough to permit bottoming of the stopper on the distal wall of the chamber and, therefore, the entire contents of the syringe cannot be fully injected. However, extending the plunger rod to the extended position by exerting an axial force to the plunger rod in the proximal direction will allow the first plunger rod piece to slide relative to the second plunger rod piece to extend the length of the plunger rod, prior to injection. In the extended position, the stopper of the plunger rod will contact the distal wall of the chamber and therefore, all of the contents of the syringe will be injected.

Figure 14:
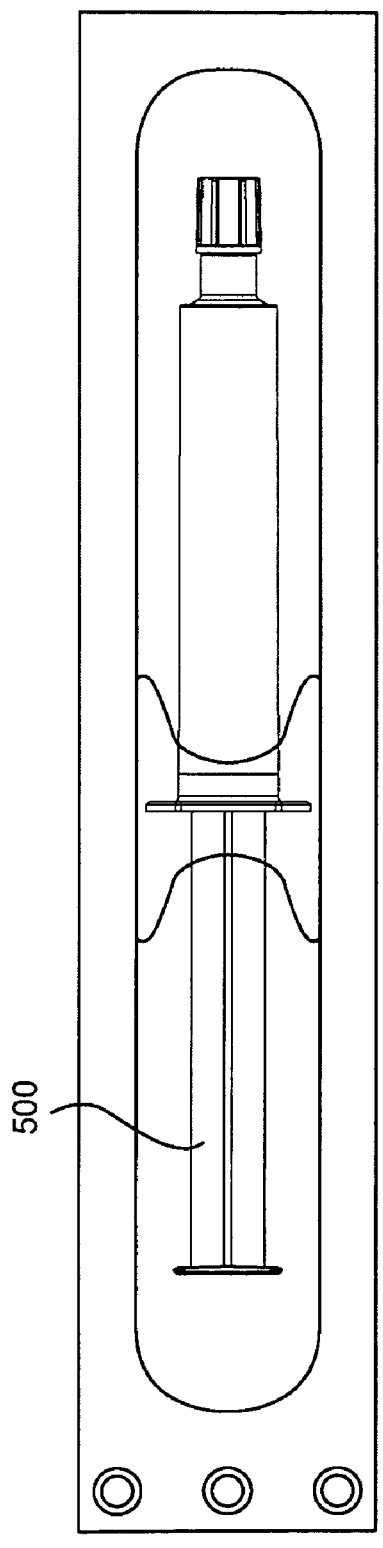
FIG. 14 shows a packaged syringe according to the prior art.

In many instances, syringes are stored in packaging when shipped to users such as hospitals and other medical facilities. Moreover, many syringes can also be pre-filled and therefore, the syringe is not shipped with the plunger rod fully advanced distally with the stopper bottomed out against the distal wall of the syringe. To the contrary, many pre-filled syringes that are filled with a fluid such as a flush solution or a medication are shipped with the stopper of the plunger rod positioned at the proximal end of the syringe barrel such that the plunger rod protrudes out the proximal end of the barrel. Therefore, with a single piece plunger rod assembly of the prior art, as shown in FIG. 14, the packaging must accommodate for these syringes and the elongate plunger rods 500. Such a device requires a relatively long package and large amount of packaging material to accommodate the syringe. Additionally, the overall length of the syringe in FIG. 14 occupies more space, which would occupy additional space in the medical facility. The additional packaging material for the longer syringe results in additional waste to be disposed of after use of the syringe.

Figure 15:
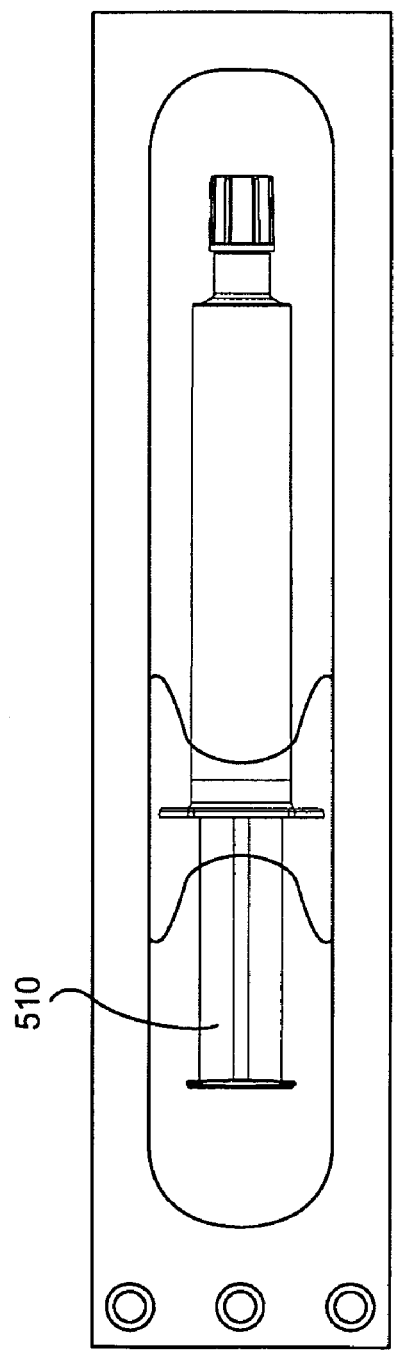
FIG. 15 shows a packaged syringe according to an embodiment of the invention.

According to one or more embodiments of the present invention, the two piece plunger rod can be utilized to conserve packaging or space occupied by the packaged device. This is particularly useful for pre-filled syringes that are pre-filled with fluids such as flush solutions or medications. As shown in FIG. 15, by providing a plunger rod 510 which can be stored or packaged in a compressed position when the stopper at the distal end of the plunger rod is located at the proximal end of the syringe barrel and the plunger rod extending out the proximal end of the barrel, the overall length of the packaged product and amount of packaging material required to package the product is significantly reduced. Thus, according to one or more embodiments, less space is occupied during storage, less packaging material is used for packaged syringes, and less waste is generated after use of a packaged syringe.

One or more aspects of the present invention provide for a method of using a pre-filled syringe according to one or more of the embodiments disclosed herein. According to one or more embodiments, the pre-filled syringe is packaged with a stopper disposed within the syringe barrel wherein the stopper forms a seal with the inside surface at the proximal of the barrel. A plunger rod is attached to the stopper, and a substantial portion of the plunger rod extends outside the syringe barrel. Locking elements disposed on the plunger rod pieces according to embodiments described herein are engaged to lock the plunger rod in the compressed position. According to one embodiment, preparing the syringe for use or injection includes removing the pre-filled syringe from the packaging; applying an initial axial force to the one plunger rod pieces in the proximal direction so the locking element of the first plunger rod piece of the plunger rod disengages from the locking element of the second plunger rod piece of the plunger rod; and applying a continuous axial force to the plunger rod in the proximal direction so a locking element of the first plunger rod piece engages with a locking element of the second plunger rod piece. Further embodiments include injecting or expelling of the contents of the syringe by applying a continuous axial force on the plunger rod in the distal direction until the stopper is in contact with the distal wall of the syringe or bottomed. The fluid injected or expelled according to one or more embodiments includes a medical flush solution. Further embodiments provide for method of using a syringe prefilled with fluid comprising medication.

A further aspect of the invention includes a method for packaging a pre-filled syringe described herein. According to one or more embodiments, preparation of a prefilled syringe assembly for packaging includes attaching a tip cap to the collar of a syringe barrel to close or cover the opening in the distal wall of the chamber, and filling the chamber of the barrel with fluid. The method further includes preparing the plunger rod-stopper assembly by positioning a two piece plunger rod having a first plunger rod piece and a second plunger rod piece in the compressed position by applying an axial force in the proximal direction until a locking element of the first plunger rod piece engages with the locking element of a second plunger rod piece, attaching a stopper to the compressed plunger rod, and inserting the plunger rod-stopper assembly into the chamber of the syringe barrel so the stopper forms a seal with the inside surface of the chamber and the amount of air within the chamber is minimized. According to one or more embodiments, the method of packaging further includes placing the pre-filled syringe in packaging in the compressed position. In a specific embodiment, the fluid is a medical flush solution. In a more specific embodiment, the fluid comprises medication.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical device comprising:
    a syringe barrel having a side wall with an inside surface defining a chamber for retaining fluid, an open proximal end and a distal end including a distal wall having a passageway therethrough in fluid communication with the chamber, the chamber being pre-filled with a fluid;
    an elongate plunger rod disposed within the barrel and having proximal and distal ends, the plunger rod comprising a first plunger rod piece comprising a frame defining a cross-shaped hollow receptacle and a second plunger rod piece having a cross-shaped cross section that is complementary to the first plunger rod piece, the first plunger rod piece being slidably disposed about the second plunger rod piece thereby permitting the overall length of the plunger rod to be reversibly adjustable between a compressed length to an extended length; and
    a stopper having a proximal end and a distal end, the stopper attached to the distal end of the plunger rod, the medical device being operable to expel fluid upon extending the first and second plunger rod pieces of the plunger rod to the extended length and application of an axial force to the plunger rod in a distal direction.

2. The medical device of claim 1, wherein the first plunger rod piece and the second plunger rod piece are moveable from the compressed length to the extended length by application of an axial force.

3. The medical device of claim 1, wherein the first plunger rod piece and the second plunger rod piece are moved from the compressed length to the extended length by motion substantially free of rotational forces.

4. The medical device of claim 1, further comprising a first locking element on the first plunger rod piece and a second locking element on the second plunger rod piece, the first and second locking elements cooperating to reversibly fix the plunger rod in the extended length.

5. The medical device of claim 4, wherein the first locking element comprises a projection extending outwardly from the first plunger rod piece and the second locking element comprises an opening in the second plunger rod piece adapted to receive the projection and preventing further relative movement of the plunger rod pieces.

6. The medical device of claim 3, further comprising a package, wherein the syringe, the plunger rod and the stopper are assembled and the plunger rod is in the compressed position.

7. The medical device of claim 6, wherein the fluid comprises a medical flush solution.

8. The medical device of claim 6, wherein the fluid comprises a medication.

9. The medical device of claim 6, further comprising a locking means for slidably locking the plunger rod to the extended length.

10. A medical device comprising:
    a syringe including a barrel prefilled with a fluid for delivery to a patient or a medical device; and
    a plunger rod disposed within the barrel, the plunger rod comprising a proximal portion defining a cross-shaped hollow receptacle having a cross-shaped cross section and a distal portion having a cross-shaped cross section that is complementary to the proximal portion, the distal portion and the proximal portion being slidably coupled such that the overall length of the plunger rod is slidably adjustable between a compressed length and an extended length, the plunger rod being operable to expel the fluid when placed in the extended length.

11. The medical device of claim 10 wherein one of the proximal and distal portions includes detents and the other of the proximal and distal portions includes a recess or opening configured to receive the detents, the detents and recess or opening being positioned to permit the length of the plunger rod to be adjusted.

12. The medical device of claim 10, wherein the distal portion is slidably received within the proximal portion.

13. The medical device of claim 11, wherein the detents comprise projections that are biased radially outwardly to engage the recess or opening.

14. The medical device of claim 10, wherein the device is enclosed in packaging.

15. The medical device of claim 10, further comprising a locking means for slidably locking the plunger rod to the extended length.

16. The medical device of claim 10, wherein the overall length of the plunger rod is reversibly adjustable between the compressed length and the extended length.

17. The medical device of claim 1, wherein the first plunger rod piece comprises a proximal portion of the plunger rod and the second plunger rod piece comprises a distal portion of the plunger rod, the distal portion being slidably received within the proximal portion.

* * * * *